(12) United States Patent
Sakaguchi et al.

(10) Patent No.: US 7,937,777 B2
(45) Date of Patent: May 10, 2011

(54) DISPOSABLE WEARING ARTICLE

(75) Inventors: Satoru Sakaguchi, Kagawa-ken (JP);
Hiroki Ishikawa, Kagawa-ken (JP)

(73) Assignee: Uni-Charm Corporation, Ehime (JP)

( * ) Notice: Subject to any disclaimer, the term of this patent is extended or adjusted under 35 U.S.C. 154(b) by 992 days.

(21) Appl. No.: 11/074,640

(22) Filed: Mar. 9, 2005

(65) Prior Publication Data
US 2005/0203479 A1    Sep. 15, 2005

(30) Foreign Application Priority Data

Mar. 12, 2004   (JP) .................................. 2004-70343

(51) Int. Cl.
*A41B 9/00* (2006.01)
(52) U.S. Cl. ............................. 2/400; 2/404; 604/385.11
(58) Field of Classification Search .............. 2/400, 404; 604/385.11
See application file for complete search history.

(56) References Cited

U.S. PATENT DOCUMENTS

| 5,843,057 | A  | * | 12/1998 | McCormack | 604/367 |
| 6,240,569 | B1 | * | 6/2001 | Van Gompel et al. | 2/400 |
| 6,454,752 | B1 | * | 9/2002 | Huang et al. | 604/389 |
| 6,676,647 | B2 | * | 1/2004 | Shimada et al. | 604/385.11 |
| 2005/0010186 | A1 | | 1/2005 | Otsubo et al. | |

FOREIGN PATENT DOCUMENTS

| EP | 00556749 A1 | 2/1993 |
| JP | 3-16920 | 2/1991 |
| JP | 5-228177 | 9/1993 |
| JP | 2003-390284 | 10/2003 |

* cited by examiner

*Primary Examiner* — Gary L Welch
*Assistant Examiner* — Alissa J Tompkins
(74) *Attorney, Agent, or Firm* — Lowe, Hauptman, Ham & Berner, LLP

(57) ABSTRACT

A disposable wearing article has a front waist covering panel, a rear waist covering panel and a crotch covering panel, a body facing sheet and an undergarment facing sheet in the front and rear waist covering panels are elastically stretchable in a waist-surrounding direction. These sheets are made of nonwoven fabrics and have regions in which these sheets are placed upon each other and the undergarment facing sheet repetitively undulates in the waist-surrounding direction to form a plurality of gathers.

17 Claims, 8 Drawing Sheets

DISPOSABLE WEARING ARTICLE

RELATED APPLICATIONS

The present application is based on, and claims priority from, Japanese Application Number 2004-70343, filed Mar. 12, 2004, the disclosure of which is hereby incorporated by reference herein in its entirety.

BACKGROUND OF THE INVENTION

The present invention relates to a disposable wearing article suitable to be used as a disposable diaper, training pants, pants for incontinent patient or the like.

Disposable briefs disclosed in Japanese Unexamined Utility Model Application Publication No. 1991-16920 (hereinafter referred to as "Citation") comprise a topsheet, a backsheet and an absorbent core interposed between these sheets wherein the top- and backsheets are made of elastic nonwoven fabrics.

In the case of the briefs disclosed in Citation, the top- and backsheets made of elastic nonwoven fabrics are generally expensive compared to those made of inelastics nonwoven fabric and inevitably the material cost for such briefs is driven up. To alleviate such cost drive, it may be contemplated, for example, to use elastic nonwoven fabrics having a relatively low basis weight. However, the lower the basis weight is, the more distinctly the wearer's skin is seen through such nonwoven fabrics.

SUMMARY OF THE INVENTION

It is an object of the present invention to provide a disposable wearing article using elastically stretchable nonwoven fabrics in waist covering regions improved so that the wearer's skin can not be seen through the article even when a basis weight of the nonwoven fabrics is relatively low.

According to the present invention, there is provided a disposable wearing article comprising: a front waist covering panel, a rear waist covering panel and a crotch covering panel cooperating together to form a waist-hole and a pair of leg-holes, each of the front and rear waist covering panels at least partially comprising a body facing sheet and an undergarment facing sheet, each of these sheets being elastically stretchable in a waist-surrounding direction of the article.

The article further comprises the two sheets being respectively formed of nonwoven fabrics and have regions in which the two sheets are placed upon each other and at least the undergarment facing sheet of the two sheets defining the regions repetitively undulating in the waist-surrounding direction to form a plurality of gathers in an intermediate zone defined between the waist-hole and the leg-holes.

In such a wearing article, the undergarment facing sheet placed upon the body facing sheet is formed with a plurality of gathers and a percentage of luminous rays going straight from the wearer's skin through the body sheet and the undergarment facing sheet toward eyes of a person other than the wearer is lower from the regions having a plurality of gathers than from the flat regions having none of gathers. Thus, these gathers effectively protect the wearer's skin from being distinctly seen through the article even when the basis weight of the undergarment facing sheet and the body facing sheet is relatively low.

According to one preferred embodiment of the invention, a plurality of band-like elastic spacers extending in parallel one to another in the waist-surrounding direction are interposed between the two sheets in the intermediate zone.

In the wearing article according to this embodiment, the elastic spacers function as spacers adapted to space the body facing sheet and the undergarment facing sheet from each other and thereby to protect the wearer's skin from being distinctly seen through the article even when the gathers of the undergarment facing sheet are flattened.

According to another preferred embodiment of the invention, the nonwoven fabric forming said two sheets have a fineness in a range of 0.1 to 7 dtx and a basis weight in a range of 10 to 30 g/m².

According to this embodiment, it is ensured that the wearer's skin is reliably protected from being distinctly seen through the article even when the undergarment facing sheet and the body facing sheet are formed of nonwoven fabrics having such a low fineness and such a low basis weight.

In any of the aforesaid embodiments, an absorbent region such as, for example, an absorbent body is provided in at least the crotch covering region, if necessary.

DETAILED DESCRIPTION OF THE PREFERRED EMBODIMENTS

Details of a disposable wearing article according to the present invention will be more fully understood from the description given hereunder with reference to the accompanying drawings.

Figure 1:
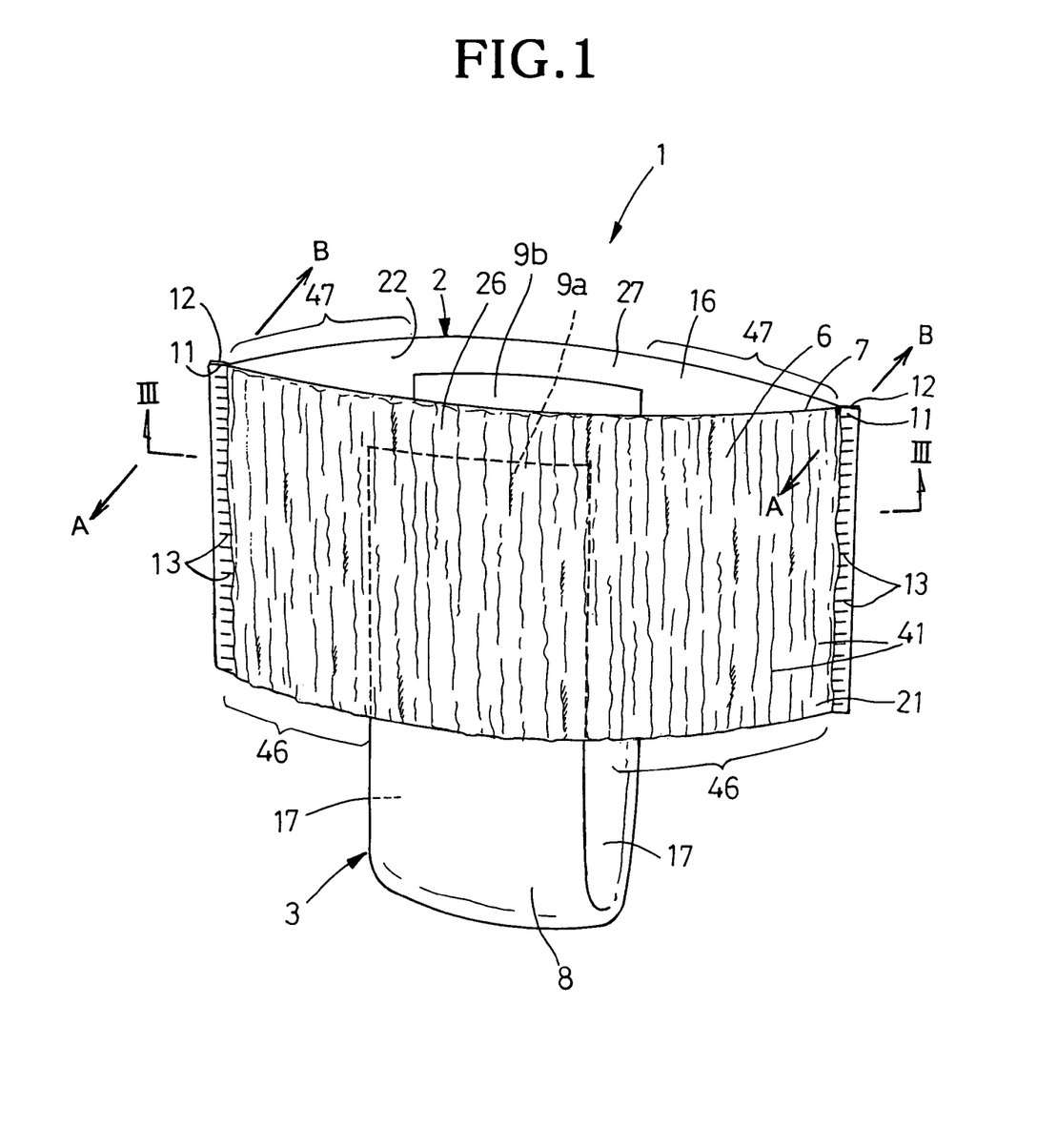
FIG. 1 is a perspective view showing a disposable diaper as a typical embodiment of the invention.

A disposable diaper 1 shown in FIG. 1 in a perspective view is of pants-type and comprises a waist covering panel 2 which is annular as viewed in FIG. 1 and a crotch covering panel 3 which is U-shaped as viewed in FIG. 1. The waist covering panel 2 comprises a front waist covering panel 6 and a rear waist covering panel 7. These waist covering panels 6, 7 are overlapped and joined together along transversely opposite lateral edges 11, 12 of the respective waist covering panels 6, 7 at joining spots 13 arranged intermittently in a vertical direction as viewed in FIG. 1. The crotch covering panel 3 comprises a crotch covering region 8 and front and rear extension regions 9a, 9b (See FIG. 2 also) lying above the crotch covering region 8. These extension regions 9a, 9b are joined to an inner surface of the front waist covering panel 6 and to an inner surface of the rear waist covering panel 7, respectively, by means of adhesives 37 (See FIG. 3). In such a diaper 1, the front waist covering panel 6 cooperates with the rear waist covering panel 7 to form a waist-hole 16 while these waist covering panels 6, 7 cooperate with the crotch covering panel 8 to form a pair of leg-holes 17.

Figure 2:
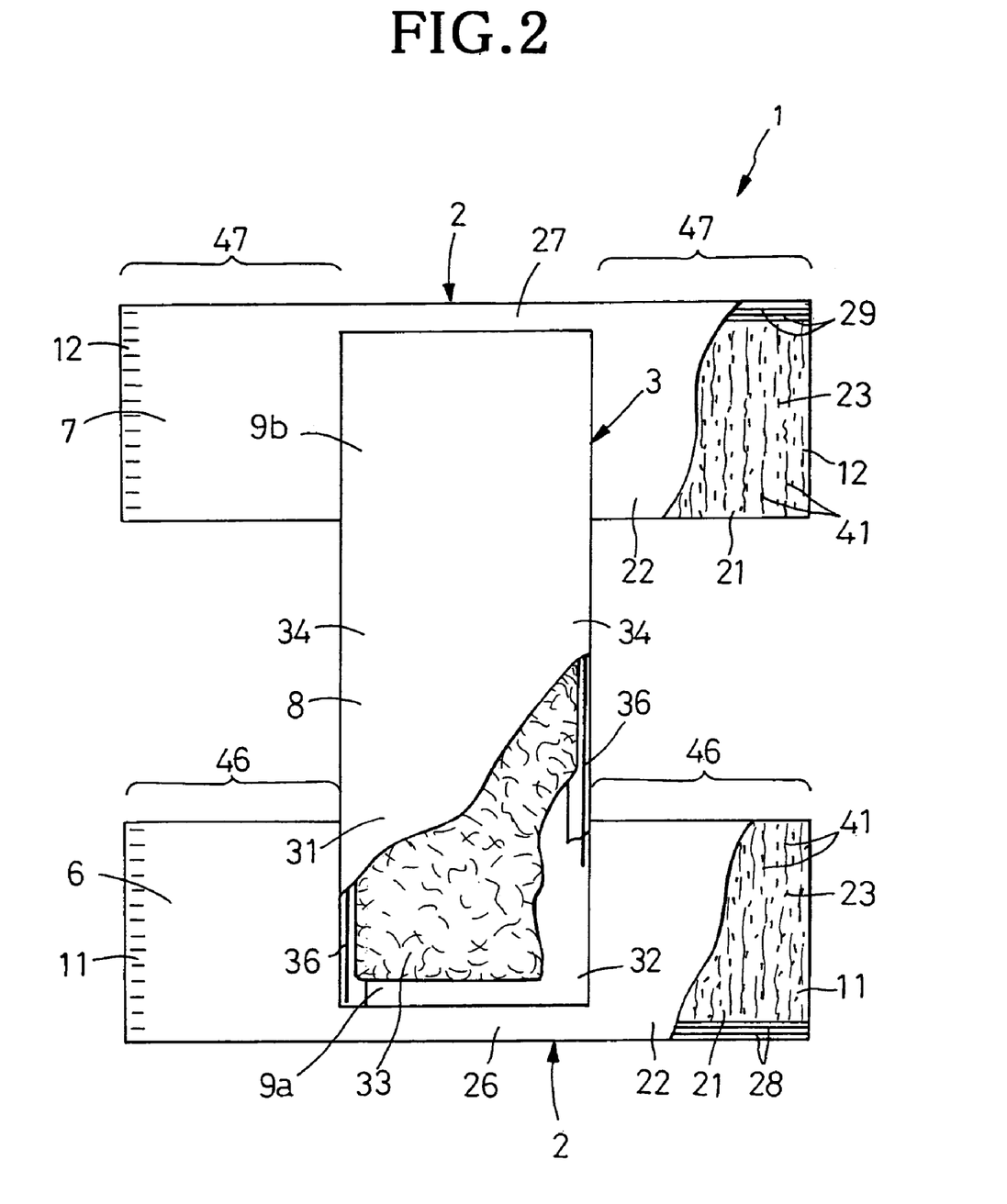
FIG. 2 is a partially cutaway, developed plan view of the disposable diaper.

FIG. 2 is a partially cutaway, developed plan view showing the diaper 1 with the front and rear waist covering panels 6, 7 having been peeled off from each other along the transversely opposite lateral portions 11, 12 at the joining spots 13 and developed forward as indicated by an arrow A and rearward as indicated by an arrow B. The front and rear waist covering panels 6, 7 constituting the waist covering panel 2 respectively comprise an outer sheet 21 facing the wearer's undergarment and an inner sheet 22 facing the wearer's body when the diaper 1 is put on the wearer. These outer and inner sheets 21, 22 are made of nonwoven fabrics adapted to be elastically stretchable in a waist-surrounding direction of the diaper and joined to each other intermittently in the waist-surrounding direction by means of adhesives 23 or a appropriate welding technique. Referring to FIG. 1, upper edge portions 26, 27 of the front and rear waist covering panels 6, 7 define a peripheral portion of the waist-hole 16. Along these upper edge portions 26, 27, a plurality of waist-surrounding elastic members 28, 29 are interposed between the outer sheet 21 and the inner sheet 22 and joined to at least one of these sheets 21, 22 by means of adhesives (not shown).

The crotch covering panel 3 has a rectangular shape and comprises a liquid-pervious topsheet 31, a liquid-impervious backsheet 32 and a liquid-absorbent core 33 interposed between these sheets 31, 32 so as to define the crotch covering region 8, the front extension region 9a and the rear extension region 9b. Portions of the top- and backsheets 31, 32 extending outward beyond a peripheral edge of the core 33 are joined to each other by means of adhesives (not shown). Along transversely opposite lateral portions 34 of the crotch covering panel 3 outside the core 33, leg-surrounding elastic members 36 extend along the core 33 in the vertical direction as viewed in FIG. 2 and are secured in a stretched state to the inner surface (See FIG. 3) of the topsheet 31 by means of adhesives (not shown).

Figure 3:
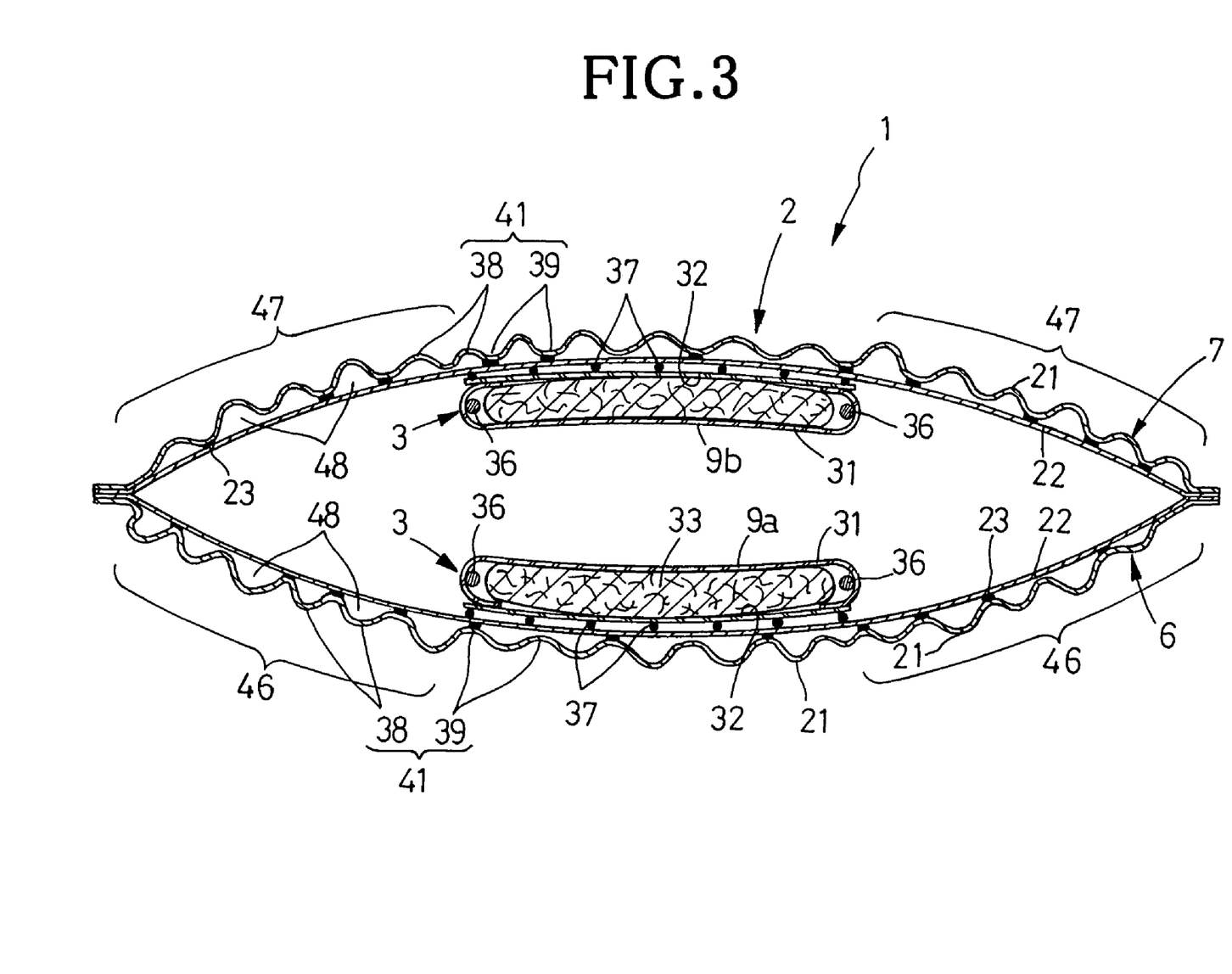
FIG. 3 is a sectional view taken along the line III-III in FIG. 1.

FIG. 3 is a sectional view taken along the line III-III in FIG. 1. The crotch covering panel 3 lies inside the waist covering panel 2 which is annular as seen in FIG. 3 and, in the front and rear extension regions 9a, 9b, the backsheet 32 is joined to the inner sheet 22 in the front and rear waist covering panels 6, 7 by means of adhesives 37. Of the waist covering panel 2, the inner sheet 22 flatly extends in the waist-surrounding direction of the diaper 1 while the outer sheet 21 undulates in the waist-surrounding direction to form a plurality of gathers 41 comprising crests 38 and troughs 39 (See FIG. 1). Such outer sheet 21 is joined to the inner sheet 22 at least along certain of the troughs 39 by means of adhesives 23 or an appropriate welding technique.

The outer and inner sheets 21, 22 are made of nonwoven fabrics which are elastically stretchable in the waist-surrounding direction, more preferably made of nonwoven fabrics having a fineness in a range of 0.1 to 7 dxt and a basis weight in a range of 10 to 30 g/m$^2$. These nonwoven fabrics are elastically stretchable at a ratio in a range of 1.5 to 3 in the waist-surrounding direction. The definition used herein, "the respective nonwoven fabrics forming the outer sheet 21 and the inner sheet 22 are elastically stretchable" means that these nonwoven fabrics quickly, e.g., within at least 5 seconds contract to 1.1-fold of the respective initial lengths thereof upon relaxation after these nonwoven fabrics have been stretched to 1.5-fold of its initial length. To obtain the front and rear waist covering panels 6, 7 each comprising the outer and inner sheets 21, 22, the inner sheet 22 dimensioned to have the same size as each of these waist covering panels 6, 7 may be stretched in the waist-surrounding direction by a given percentage not beyond the limit allowing for elastic restoration, e.g., m % and then the outer sheet 21 having, in its state not stretched at all or stretched in the waist-surrounding direction by a percentage lower than the stretched percentage (m %) for the inner sheet 22, the same size as the stretched inner sheet 22 may be joined to the inner sheet 22 intermittently in the waist-surrounding direction. For example, the outer sheet 21 having, in its state not stretched at all or stretched by 1.2-fold to 1.7-fold (i.e., 20 to 70%) in the waist-surrounding direction, having the same size as the inner sheet 22 stretched by two-fold (i.e., 100%) may be joined to such stretched inner sheet 22 using adhesives or a suitable welding technique intermittently in the waist-surrounding direction and then the inner sheet 22 may be left contract to obtain the front and rear waist covering panels 6, 7 comprising the inner sheet 22 and the outer sheet 21 joined to the inner sheet 22 and formed with the gathers 41 formed as the outer sheet 21 contracts. The crotch covering panel 3 may be joined to the inner sheet 22 in these front and rear waist covering panels 6, 7 to obtain the diaper 1 as illustrated by FIG. 2 in its developed state. The waist-surrounding elastic members 11, 12 may be previously secured in a stretched or non-stretched state to the inner sheet 22.

With such diaper 1 put on the wearer's body, portions of the inner sheet 22 lying along the transversely opposite lateral portions 46, 47 (See FIGS. 1 and 2) of the front and rear waist covering panels 6, 7 free from the crotch covering panel 3 placed upon the inner sheet 22 may be closely placed against the wearer. The outer sheet 21, on the other hand, is spaced apart from the inner sheet 22 along the respective crests 38 and thereby to form air gaps 48. Luminous rays directed from the wearer's skin through the inner and outer sheets 22, 21 to the exterior of the diaper 1 specifically passes through the inner sheet 22 into the air gaps 48 and then passes through the outer sheet 21 to be incident on the eyes of persons other than the wearer. The percentage of such luminous rays directed straight from the wearer's skin to the eyes of the persons other than the wearer and causing the wearer's skin to be seen through the diaper 1 is believed to be significantly reduced by the presence of the air gaps 48 compared to the case in which the waist covering panel 2 is formed with none of the air gaps 48. As an advantageous result, it is ensured that the wearer's skin is protected from being seen through the diaper 1 put on the wearer. Exemplary cases in which the waist covering panel 2 of the diaper 1 is formed with none of the air gaps 48 include a case in which the waist covering panel 2 comprises a single nonwoven fabric layer having a basis weight equal to the sum of a basis weight of the outer sheet 21 and a basis weight of the inner sheet 22 and a thickness equal to the sum of a thickness of the outer sheet 21 and a thickness of the inner sheet 22 instead of forming the waist covering panel 2 by two nonwoven fabrics, and a case in which, referring to FIG. 3, the inner sheet 22 is stretched in the waist-surrounding direction until the crests 38 of the outer sheet 21 are flattened and then the inner sheet 22 is closely placed against such flattened outer sheet 21. In the case of the illustrated diaper 1, on the contrary, it is unlikely that the stretchability of the waist covering panel 2 in the waist-surrounding direction might be readily reach the limit as the waist covering panel 2 made of a non-stretchable nonwoven fabric has been the case, even if the waist covering panel 2 is stretched in the waist-surrounding direction until the outer sheet 21 and the inner sheet 22 are closely placed against each other. Therefore, there is no anxiety that the waist covering panel might cause the wearer to experience a feeling of compression even when the wearer has a relatively large circumference of waist.

Figure 4:
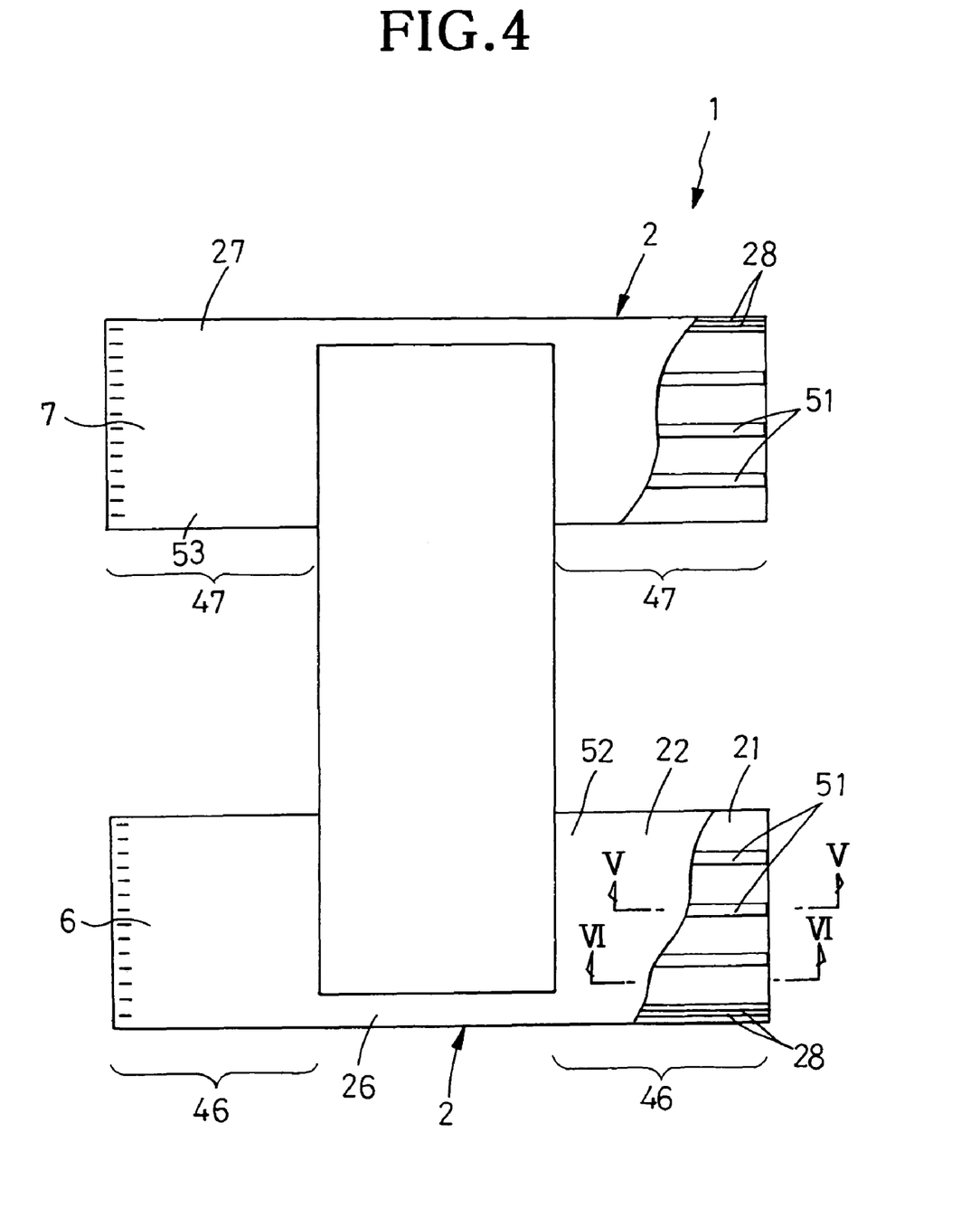
FIG. 4 is a view similar to FIG. 2, showing one preferred embodiment of the invention.
Figure 5:
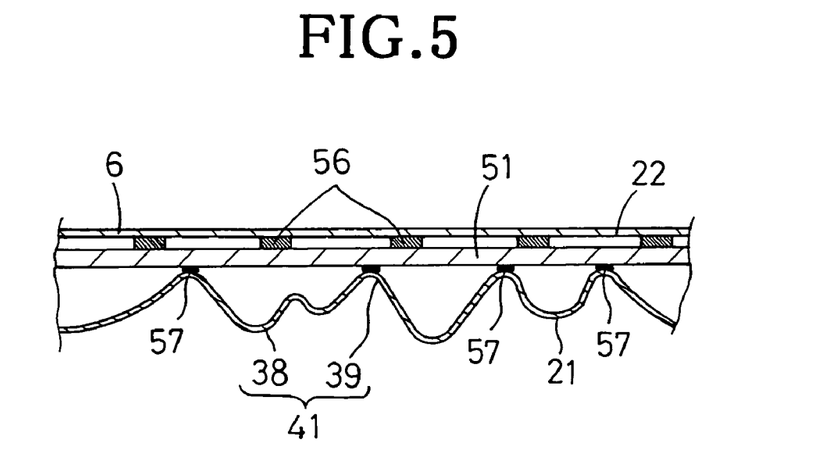
FIG. 5 is a sectional view taken along the line V-V in FIG. 4.
Figure 6:
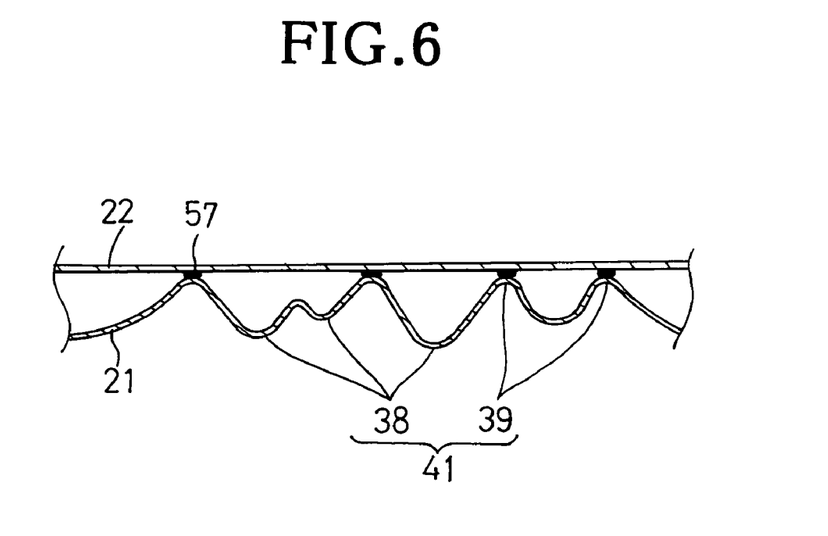
FIG. 6 is a sectional view taken along the line VI-VI in FIG. 4.

FIG. 4 is a view similar to FIG. 2, showing one preferred embodiment of the invention, FIG. 5 is a sectional view taken along the line V-V in FIG. 4 and FIG. 6 is a sectional view taken along the line VI-VI in FIG. 4. In this diaper 1, the front and rear waist covering panels 6, 7 are identical in construction and include the outer sheet 21 and the inner sheet 22. Both the outer sheet 21 and the inner sheets 22 are made of nonwoven fabrics which are elastically stretchable in the waist-surrounding direction. The outer sheet 21 undulates in the waist-surrounding direction to define a plurality of gathers 41 comprising the crests 38 and the troughs 39 while the inner sheet 22 flatly extends in the waist-surrounding direction. Along the upper edge portions 26, 27 of the front and rear waist covering panels 6, 7 defining a peripheral portion of the waist-hole 16, a plurality of waist-surrounding elastic members 28 extending in the waist-surrounding direction are interposed between the outer sheet 21 and the inner sheet 22 and secured to the inner sheet 22. In the front waist covering panel 6, one or more spacers 51 formed by elastically stretchable bands are laid in an intermediate zone defined between the edge portion 26 and an inner edge portion 52 forming a part of the leg-holes 17 so as to extend in the waist-surrounding direction and secured in a non-stretched state to the inner sheet 22 by means of adhesives 56. In the front waist covering panel 6 also, one or more spacers 51 formed by elastically stretchable bands are laid in an intermediate zone defined between the edge portion 27 and an inner edge portion 53 forming a part of the leg-holes 17 so as to extend in the waist-surrounding direction and secured in a non-stretched state to the inner sheet 22 by means of adhesives 56. The outer sheet 21 is joined by means of the adhesive 57 not only to the inner sheet 22 (FIG. 6) but also to the respective spacers 51 (FIG. 5). The adhesives 56/57 are arranged intermittently in the waist-surrounding direction (FIGS. 5,6).

Figure 7:
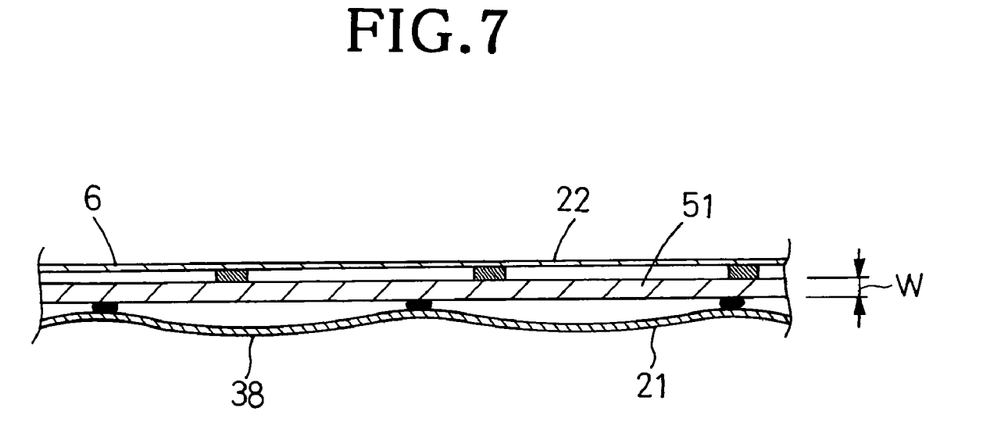
FIG. 7 is a view similar to FIG. 5, but showing the diaper in a stretched state.

FIG. 7 is a view similar to FIG. 5, but showing the diaper 1 with the front waist covering panel 6 stretched in the waist-surrounding direction. While the crests 38 of the outer sheet 21 are flattened and consequently the outer sheet 21 is gradually flattened as the inner sheet 22 and the spacers 51 are integrally stretched in the waist-surrounding direction, the presence of the spacers 51 interposed between the outer and inner sheets 21, 22 maintains these sheets 21, 22 spaced apart from each other at least by a thickness W of the spacers 51 as will be apparent from the sectional view of FIG. 7. In the diaper 1 constructed as illustrated in FIGS. 4 through 7, even when the waist covering panel 2 is stretched in the waist-surrounding direction at a relatively high ratio, a possibility that the wearer's skin might be seen through the diaper 1 at the transversely opposite lateral portions 46, 47 of the waist covering panel 2 is substantially lower than the case of the diaper 1 constructed as illustrated in FIGS. 1 through 3. The spacers 51 advantageously functioning in this manner may be formed of elastic bands made of elastomer such as natural rubber, synthetic rubber or polyurethane foam. The thickness W of the spacers 51 is preferably in a range of 0.3 mm to 3 mm, more preferably in a range of 0.5 to 2 mm. Width of the spacers 51 is preferably in a range of 0.5 to 3 mm.

Figure 8:
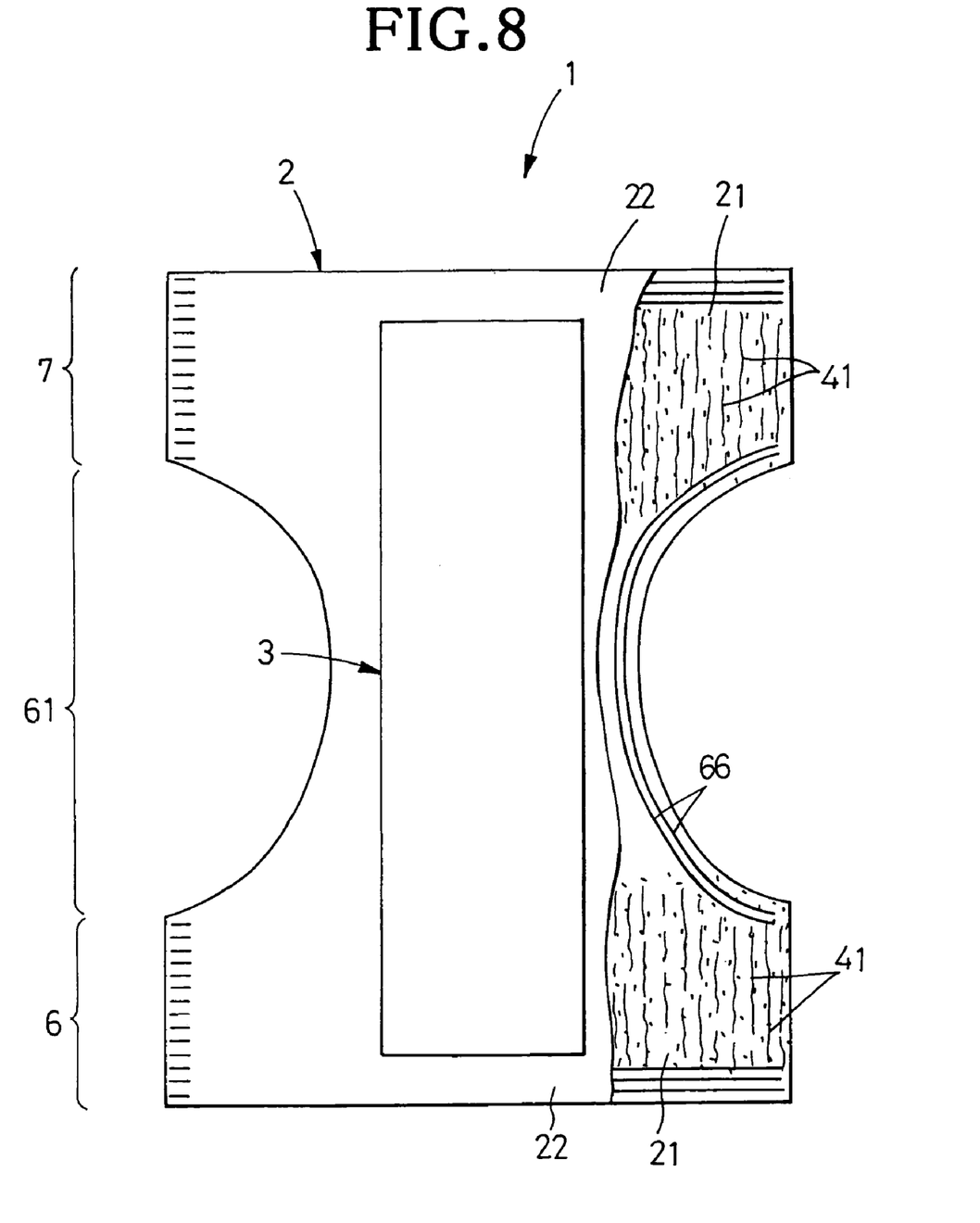
FIG. 8 is a view similar to FIG. 2, showing another preferred embodiment of the invention.

FIG. 8 is a view similar to FIG. 2, showing another embodiment of the invention. In this diaper 1, both the outer sheet 21 and the inner sheet 22 constituting the waist covering panel 2 are hourglass-shaped and joined to each other by means of adhesives 21 coated in a dotted pattern. These two sheets 21, 22 define, in addition to the front waist covering panel 6 and the rear waist covering panel 7, a crotch covering panel 61 extending between these two covering panels 6, 7. Along transversely opposite lateral portions of the crotch covering panel 61, leg-surrounding elastic members 66 extending so as to describe circular arcs are joined in a stretched or non-stretched state to the inner sheet 22. The waist covering panel 2 of the diaper 1 according to this embodiment also can be obtained by joining the elastically stretchable outer sheet 21, for example, in a non-stretched state, to the inner sheet 22 elastically stretched in the transverse direction of the diaper 1 and then allowing the inner sheet 22 to contract. Such outer sheet 21 is formed substantially over its entire area with gathers 41. The present invention may be alternatively implemented by interposing the crotch covering panel 3 between the outer sheet 21 and the inner sheet 22.

Figure 9:
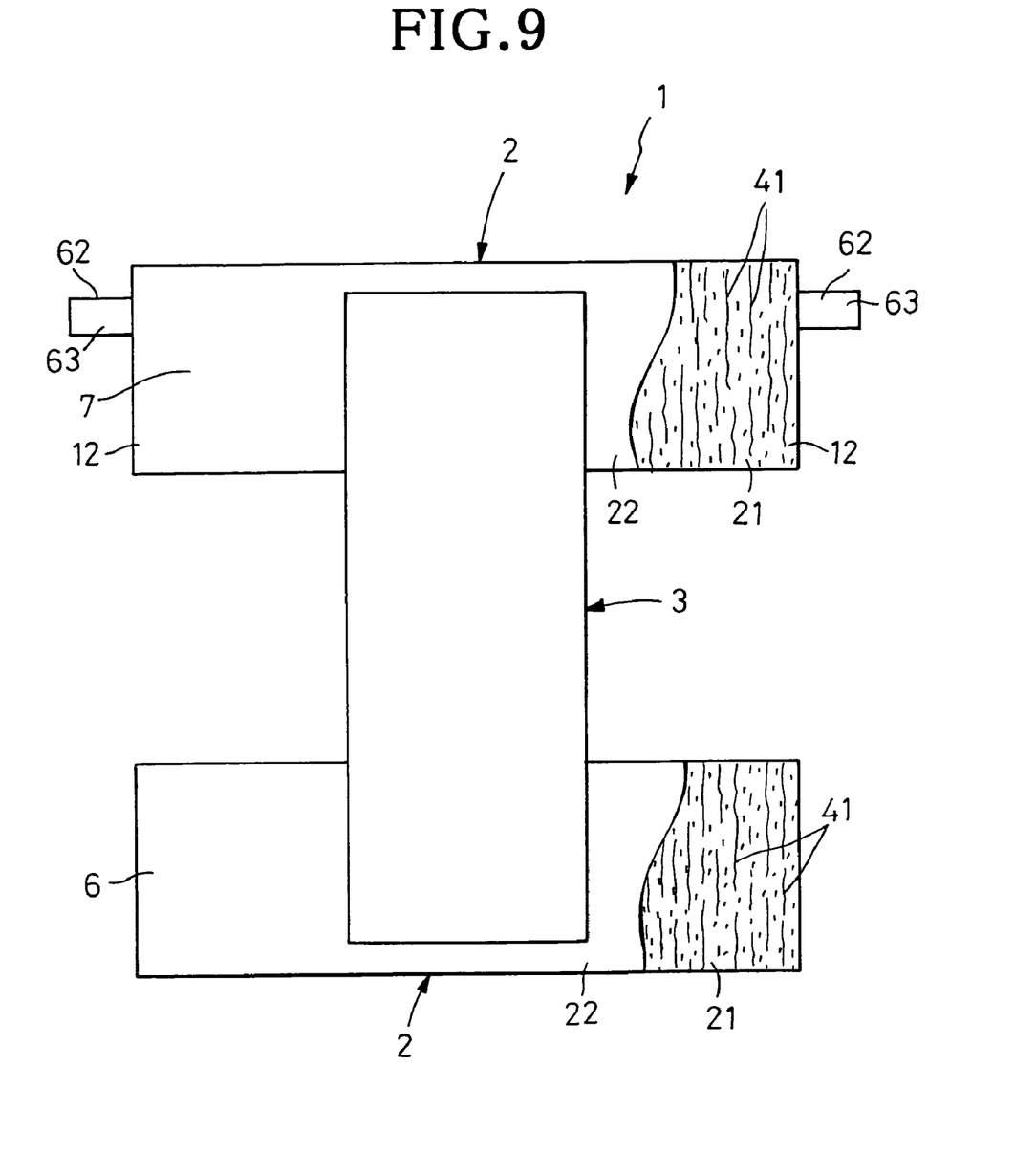
FIG. 9 is a view similar to FIG. 2, showing still another preferred embodiment of the invention.

FIG. 9 is a view similar to FIG. 2, showing still another preferred embodiment of the invention. This diaper 1 is not of pants-type like the diaper 1 shown in FIG. 1 but of open-type. While this diaper 1 also comprises the waist covering panel 2 and the crotch covering panel 3 both having the same constructions as those in FIG. 2 wherein the outer sheet 21 of the waist covering panel 2 is formed with a plurality of gathers 41, this diaper 1 further comprises tape fasteners 62 attached to the transversely opposite lateral portions 12 of the rear waist covering panel 7 so that these tape fasteners 62 extend outward of the diaper 1. The diaper 1 may be put on the wearer by placing the front and rear waist covering panels 6, 7 against the wearer's front and rear waist regions and then releasably anchoring the tape fasteners 63 on the outer sheet 21 of the front waist covering panel 6 while at least one of these waist covering panels 6, 7 is stretched in the waist-surrounding direction. The tape fasteners 62 may be coated on respective inner surfaces 63 thereof with a pressure-sensitive adhesive or may be provided on these inner surfaces 63 with a hook member of a so-called mechanical fastener comprising a plurality of hooks adapted to be detachably engaged with the nonwoven fabric constituting the outer sheet 21 or a target zone provided on the outer sheet 21.

Without departing from the scope of the invention, any one of the front and rear waist covering panels 6, 7 having the construction as exemplarily shown in FIG. 2 may be replaced by a single layer of a nonwoven fabric or a plastic film or a composite sheet, for example, consisting of a nonwoven fabric and a plastic film. Furthermore, it is also possible to replace any one of these waist covering panels 6, 7 by that which is not elastically stretchable in the waist-surrounding direction. In addition, the present invention may be implemented without the waist-surrounding elastic members 28 and/or 29 and the absorbent core 33.

The present invention is applicable to produce the wearing article such as the disposable diaper free from the anxiety that the wearer's skin might be seen through the article in the front and rear waist covering panels thereof.

What is claimed is:

1. A disposable wearing article, comprising:
   a front waist covering panel;
   a rear waist covering panel;
   a crotch covering panel;
   a waist-hole;
   a pair of leg-holes;
   each of said front and rear waist covering panels at least partially comprising a body facing sheet and an undergarment facing sheet, each of said sheets being elastically stretchable in a waist-surrounding direction of said article;
   said two sheets being respectively formed of nonwoven fabrics and have regions in which said two sheets are placed upon each other and spaced from each other by air gaps in a thickness direction of the respective waist covering panel; and
   said undergarment facing sheet of said two sheets defining said regions repetitively undulating in said waist-surrounding direction to form a plurality of gathers in an intermediate zone defined between said waist-hole and said leg-holes,
   wherein the waist covering panels are free of waist elastic members, and a peripheral edge of said waist hole is rendered elastically stretchable solely by the elasticity of said two sheets of each said front and rear waist covering panels.

2. The wearing article set forth by claim 1, wherein the nonwoven fabrics forming said two sheets have a fineness in a range of 0.1 to 7 dtx and a basis weight in a range of 10 to 30 g/m².

3. The wearing article set forth by claim 1, wherein the body facing sheet is substantially free of gathers and smother than the associated undergarment facing sheet.

4. The wearing article set forth by claim 1, wherein said gathers are formed and present throughout an entire area of the undergarment facing sheet.

5. The wearing article set forth by claim 1, wherein the body facing sheet is substantially free of gathers.

6. The wearing article set forth by claim 1, wherein
each of said front and rear waist covering panels is obtained by bonding said body and undergarment facing sheets while stretching said body facing sheet in said waist-surrounding direction without stretching said undergarment facing sheet in said waist-surrounding direction, so that the said body and undergarment facing sheets have the same size in the waist-surrounding direction.

7. The wearing article set forth by claim 1, wherein
each of said front and rear waist covering panels is obtained by bonding said body and undergarment facing sheets while stretching said body facing sheet in said waist-surrounding direction at a first stretched percentage and stretching said undergarment facing sheet in said waist-surrounding direction at a second stretched percentage lower than the first stretched percentage, so that the said body and undergarment facing sheets have the same size in the waist-surrounding direction.

8. The wearing article set forth by claim 1, wherein said body facing sheet and said undergarment facing sheet are elastically contractible, within at least 5 seconds, to 1.1 times of respective initial lengths thereof upon relaxation after said two sheets have been stretched in the waist-surrounding direction to 1.5 times of the respective initial lengths.

9. A disposable wearing article, comprising:
a front waist region, a rear waist region and a crotch region extending in a longitudinal direction of said article between said front and rear waist regions;
at least one of said front and rear waist regions comprising an elastically stretchable inner non-woven fabric adapted to face a wearer's body in use, and an elastically stretchable outer non-woven fabric adapted to face away from the wearer's body in use;
said inner and outer non-woven fabrics being elastically stretchable in a transverse direction perpendicular to the longitudinal direction of said article;
said inner and outer non-woven fabrics being placed upon each other and directly bonded to each other at a plurality of intermittently arranged bonding spots; and
a plurality of elastic spacers which are elastic bands extending in parallel one to another in said transverse direction and are interposed between said inner and outer non-woven fabrics,
wherein, when said article is in a relaxed state without being stretched by external forces, gathers are formed in the outer non-woven fabric between adjacent said bonding spots whereas the inner non-woven fabric is substantially free of gathers, said gathers defining air gaps between the outer and inner non-woven fabrics,
wherein an entirety of each of said inner and outer non-woven fabrics is elastically stretchable in the traverse direction.

10. The wearing article set forth by claim 9, wherein said gathers are present throughout an entire area of the outer non-woven fabric.

11. The wearing article set forth by claim 9, wherein said elastic spacers are intermittently bonded in a non-stretched state to said inner non-woven fabric.

12. The wearing article set forth by claim 9, wherein
said elastic spacers are directly, intermittently bonded to said inner non-woven fabric, and
when said article is in the relaxed stated, the inner non-woven fabric remains substantially gather-free despite the direct bonding of said inner non-woven fabric to said elastic spacers.

13. The wearing article set forth by claim 9, further comprising waist elastic members other than said elastic spacers and attached to end edges of said front and rear waist regions to define an elasticized peripheral edge of a waist hole of the article;
wherein said gathers are present throughout the entire area of the outer non-woven fabric, including regions that are not coexistent with the waist elastic members and the elastic spacers.

14. The wearing article set forth by claim 13, wherein said waist elastic members are bonded in a non-stretched state to said inner non-woven fabric.

15. The wearing article set forth by claim 9, wherein, when said article is in the relaxed state,
between each pair of the bonding spots that are adjacent in the transverse direction, the inner non-woven fabric is substantially flat, whereas the outer non-woven fabric describes a curve convex away from the inner non-woven fabric.

16. A disposable wearing article, comprising:
a front waist region, a rear waist region and a crotch region extending in a longitudinal direction of said article between said front and rear waist regions;
at least one of said front and rear waist regions comprising an elastically stretchable inner non-woven fabric adapted to face a wearer's body in use, and an elastically stretchable outer non-woven fabric adapted to face away from the wearer's body in use;
said inner and outer non-woven fabrics being elastically stretchable in a transverse direction perpendicular to the longitudinal direction of said article;
said inner and outer non-woven fabrics being placed upon each other and directly bonded to each other at a plurality of intermittently arranged bonding spots;
wherein, when said article is in a relaxed state without being stretched by external forces, gathers are formed in the outer non-woven fabric between adjacent said bonding spots whereas the inner non-woven fabric is substantially free of gathers, said gathers defining air gaps between the outer and inner non-woven fabrics,
wherein
end edges of said front and rear waist regions define a peripheral edge of a waist hole of the article; and
said peripheral edge of said waist hole is rendered elastically stretchable solely by the elasticity of said inner and outer non-woven fabrics.

17. The wearing article set forth by claim 16, wherein said inner and outer non-woven fabrics are elastically contractible, within at least 5 seconds, to 1.1 times of respective initial lengths thereof upon relaxation after said two fabrics have been stretched to 1.5 times of the respective initial lengths.

* * * * *